United States Patent
Yada et al.

(10) Patent No.: US 7,189,872 B2
(45) Date of Patent: Mar. 13, 2007

(54) PROCESS FOR PRODUCING (METH)ACRYLIC ACID

(75) Inventors: Shuhei Yada, Mie (JP); Kiyoshi Takahashi, Tokyo (JP); Kenji Takasaki, Mie (JP); Yasushi Ogawa, Mie (JP); Kimikatsu Jinno, Mie (JP); Yoshiro Suzuki, Mie (JP)

(73) Assignee: Mitsubishi Chemical Corporation, Tokyo (JP)

(*) Notice: Subject to any disclaimer, the term of this patent is extended or adjusted under 35 U.S.C. 154(b) by 206 days.

(21) Appl. No.: 10/864,498

(22) Filed: Jun. 10, 2004

(65) Prior Publication Data

US 2004/0225152 A1 Nov. 11, 2004

Related U.S. Application Data

(63) Continuation of application No. PCT/JP02/13021, filed on Dec. 12, 2002.

(30) Foreign Application Priority Data

Dec. 14, 2001 (JP) ............... 2001-381867

(51) Int. Cl.
C07C 51/16 (2006.01)
C07C 51/42 (2006.01)

(52) U.S. Cl. .................... 562/600; 562/523

(58) Field of Classification Search ........ 562/523, 562/529, 530, 531, 532, 598, 600
See application file for complete search history.

(56) References Cited

U.S. PATENT DOCUMENTS 6,448,438 B1 9/2002 Yada et al.
6,500,982 B1* 12/2002 Hale et al. ............... 562/600
2004/0225152 A1 11/2004 Yada et al.

FOREIGN PATENT DOCUMENTS

| CN | 1287113 A | 3/2001 |
| EP | 1065197 A1 | 1/2001 |
| JP | 8-134016 A | 5/1996 |
| JP | 2001-340701 | 12/2001 |

OTHER PUBLICATIONS

Bennett et al., Chemical Engineering Progress vol. 96, Iss. 5; May 2000, pp. 19-34.*
U.S. Appl. No. 11/434,067, filed May 16, 2006, Yada et al.

* cited by examiner

*Primary Examiner*—Thurman K. Page
*Assistant Examiner*—Karl Puttlitz
(74) *Attorney, Agent, or Firm*—Oblon, Spivak, McClelland, Maier & Neustadt, P.C.

(57) ABSTRACT

Clogging of a distillation column by polymerization caused by a change of the production rate of (meth)acrylic acid, is prevented to carry out a stabilized operation over a long period. A process for producing (meth)acrylic acid, which includes a purification step wherein a (meth)acrylic acid-containing material to be purified is supplied to and distilled by a distillation column, wherein during a cut operation in which the production rate of (meth)acrylic acid is reduced by $\alpha$% relative to the production rate of (meth)acrylic acid during the ordinary operation, the liquid/gas flow rate in the distillation column is adjusted to be at least $(100-\alpha/2)$% of the liquid/gas flow rate during the ordinary operation.

14 Claims, 1 Drawing Sheet

PROCESS FOR PRODUCING (METH)ACRYLIC ACID

CROSS REFERENCES TO RELATED APPLICATIONS

This application is a continuation of International Patent Application No. PCT/JP02/13021, filed on Dec. 12, 2002, and claims priority to Japanese Patent Application No. 2001-381867, filed on Dec. 14, 2001.

BACKGROUND OF THE INVENTION

Field of the Invention

The present invention relates to a process for producing (meth)acrylic acid. Particularly, it relates to a process for producing (meth)acrylic acid, whereby clogging of a distillation column for purifying a (meth)acrylic acid-containing liquid, is prevented thereby to carry out a stabilized operation of the distillation column over a long period.

In this specification, (meth)acrylic acid is a general term for acrylic acid and methacrylic acid and may mean one or both of them.

Acrylic acid is produced by vapor phase oxidation of propane, propylene or acrolein. The acrylic acid-containing gas obtained by the vapor phase oxidation is then contacted with water in a collection column to form an aqueous acrylic acid solution. To this aqueous acrylic acid solution, an azeotropic agent is added, and the azeotropic mixture comprising water and the azeotropic agent, is distilled, in an azeotropic agent-dehydration distillation column, whereby from the column bottom, crude acrylic acid containing acetic acid, will be recovered. Then, this crude acrylic acid is treated by a low boiling separation distillation column to separate a low boiling fraction such as acetic acid, and further a heavy fraction is removed by a high boiling separation distillation column to obtain purified acrylic acid. Further, there may be a case where an aldehyde in the obtained purified acrylic acid is converted to a heavy substance and removed as a heavy fraction in a purification distillation column for higher purification.

On the other hand, methacrylic acid is produced by using isobutylene or t-butyl alcohol as the starting material and via the same oxidation and purification process as described above.

(Meth)acrylic acid is an easily polymerizable compound, and it is well known that a polymer of (meth)acrylic acid is likely to be formed in its purification step, particularly in a distillation step where heating or vaporization is carried out. The formed polymer is likely to cause clogging of the distillation column (hereinafter sometimes referred to as "clogging by polymerization") and thus hinder the operation of the distillation column. Accordingly, it is common to take the following precaution to prevent such polymerization.

① Distillation is carried out under reduced pressure to lower the operation temperature.

② A polymerization inhibitor such as p-hydroquinone, p-methoxyphenol or phenothiazine, is added.

③ Molecular oxygen is supplied.

④ The interior of the distillation column is structured so that liquid or gas dwelling portions will scarcely be formed.

DISCUSSION OF BACKGROUND

Such a precaution to prevent the polymerization is based on a presumption that a continuous operation is carried out under a constant condition. Accordingly, the intended object can be accomplished in an ordinary operation wherein the operation is carried out at a production rate for (meth)acrylic acid as designed by installments. However, in an actual commercial plant, the operation conditions will be changed due to a change in the production rate, and also with respect to a distillation column, it is common that the operation will not be continued under the same condition. Therefore, even if the basic operation conditions may be the same, due to a change of the operation condition of the distillation column due to a change of the production rate, polymerization of (meth)acrylic acid can not be prevented by the above-mentioned precaution to prevent the polymerization, and there still has been a problem that clogging by polymerization will result.

It is an object of the present invention to provide a process for producing (meth)acrylic acid whereby a stabilized operation can be carried out over a long period by preventing clogging of the distillation column by polymerization even if the production rate for (meth)acrylic acid is changed.

SUMMARY OF THE INVENTION

The present invention provides a process for producing (meth)acrylic acid, which includes a purification step wherein a (meth)acrylic acid-containing material to be purified is supplied to and distilled by a distillation column, characterized in that during a cut operation in which the production rate of (meth)acrylic acid is reduced by $\alpha$ % relative to the production rate of (meth)acrylic acid during the ordinary operation, the liquid/gas flow rate in the distillation column is adjusted to be at least $(100-\alpha/2)\%$ of the liquid/gas flow rate during the ordinary operation.

Here, the ordinary operation means an operation to produce (meth)acrylic acid at a production rate for (meth)acrylic acid as anticipated at the time of designing the installments for the plant for producing (meth)acrylic acid, as mentioned above.

As a result of a study on the cause for clogging of the distillation column by polymerization due to a change of the operation condition when the production rate for (meth)acrylic acid has been changed, the present inventors have found that when the liquid/gas flow rate in the distillation column changes, polymerization of (meth)acrylic acid will be accelerated, thus leading to clogging by polymerization. This is considered to be attributable to that when the liquid/gas flow rate in the distillation column changes, non-uniformity of the liquid/gas dispersion will be promoted, whereby polymerization of (meth)acrylic acid in the distillation column will be accelerated, and further a portion where clogging by polymerization is likely to result, will be formed.

Namely, in a conventional operation control method, if the production rate is reduced than the rate during the ordinary operation, the liquid/gas flow rate in the distillation column will also be reduced accordingly, and for example, when the production rate is reduced by 30%, the liquid/gas flow rate in the distillation column will also be reduced by 30%. If the liquid/gas flow rate is reduced in this manner, turbulence will be formed in the liquid/gas dispersion in the distillation column, whereby the liquid/gas dispersion will be non-uniform. And, there will be a state where polymerization of (meth)acrylic acid is likely to take place chronically, thus leading to clogging by distillation.

Further, the fluctuation of the liquid/gas flow rate in the distillation column during the production of (meth)acrylic acid may be not only a fluctuation due to such a change of the production rate, but also a fluctuation for a relatively short period of time which takes place with an interval of from a few seconds to a few tens minutes, although the average value may always be constant. In such a case, even if, in such a short period of time of a few seconds to a few minutes, there may be a state where the dispersion of the liquid or gas is inadequate, and clogging by polymerization is likely to take place locally, it will return to a state where the dispersion of the liquid or gas is sufficient, in a certain period of time, whereby there will be no serious clogging by polymerization, if the fluctuation degree and/or period is small.

According to the present invention, even during a cut operation in which the production rate is reduced than during the ordinary operation, the fluctuation of the liquid/gas flow rate in the distillation column is controlled to be small to maintain the state close to the state during the ordinary operation, thereby to prevent clogging by polymerization caused by a fluctuation of the liquid/gas flow rate.

Namely, according to the present invention, during a cut operation in which the production rate of (meth)acrylic acid is reduced by $\alpha$ % relative to the production rate of (meth)acrylic acid during the ordinary operation, the liquid/gas flow rate in the distillation column is adjusted to be at least $(100-\alpha/2)$% of the liquid/gas flow rate during the ordinary operation, whereby clogging by polymerization can effectively be prevented.

In the present invention, the liquid/gas flow rate in the distillation column means the respective weights of the liquid content and the gas content flowing in the distillation column. Namely, to adjust the liquid/gas flow rate to be constant means to adjust the liquid flow rate and the gas flow rate to be constant, and to adjust the liquid/gas flow rate to be at least $(100-\alpha/2)$% means to adjust the liquid flow rate and the gas flow rate to be at least $(100-\alpha/2)$%.

In order to maintain the liquid/gas flow rate higher than the reduction margin of the production rate even during such a cut operation, it is necessary to supply a quantity of heat corresponding to the liquid/gas flow rate to the distillation column, whereby the quantity of heat required per unit amount of the product will increase. From this viewpoint, the economical efficiency will deteriorate. However, if the operation of the distillation column becomes impossible due to clogging by polymerization, the production of (meth)acrylic acid can not be carried out, and the operation of the production line other than the distillation column also has to be stopped. And, stopping of the operation means not only that the production of (meth)acrylic acid can not be carried out, but also that there will be losses of the heat load, the labor, the product and the assisting agent, required for suspension and resumption of the operation. In consideration of these losses, it is apparent that the economical merit of capability of continuous operation of the distillation column is much larger.

In the present invention, if the operation is carried out at the above liquid/gas flow rate in a case where the production rate during the cut operation is excessively lower than the production rate during the ordinary operation, the increase of the quantity of heat for the distillation column required per unit amount of the product becomes substantial, such being not only uneconomical but also leading to a disadvantage such that the amount of recycling liquid, etc. to maintain the liquid/gas flow rate tends to be excessively large. Thus, the present invention is suitable for application to a case where the reduction of the production rate is preferably at most 30% (i.e. $\alpha \leq 30$), particularly preferably at most 25% (i.e. $\alpha \leq 25$).

In the present invention, it is preferred that the liquid withdrawn from the top and/or the bottom of the distillation column is recycled to the distillation column and/or a purification step on the upstream side thereof, so that the liquid/gas flow rate in the distillation column during the cut operation is maintained to be at the above-mentioned level.

Further, in order to suppress the fluctuation of the liquid/gas flow rate in the distillation column to be small, it is preferred to carry out a change of any operational condition influential over the liquid/gas flow rate slowly by taking time. Accordingly, when the amount of the material to be purified, supplied to the distillation column, the amount of a liquid refluxed to the distillation column, or the heat load on a riboiler of the distillation column (a heat exchanger for heating the bottom liquid of the distillation column), is changed, the change per hour (the speed of the change) is preferably at most 5%, particularly preferably at most 3%.

Further, in order to suppress the fluctuation of the liquid/gas flow rate in the distillation column even during the ordinary operation, the fluctuation margin of the heat load (the quantity of the supplied heat) on the riboiler of the distillation column is preferably controlled to be a fluctuation margin such that proportions $X_B$ and $X_A$ of the differences between an average value $R_5$ of the heat load during optional 5 minutes and an average value $R_B$ of the heat load during one hour before the 5 minutes and between $R_5$ and an average value $R_A$ of the heat load for one hour after the 5 minutes, as calculated by the following formulae, are at most 10%:

$$X_B=(|R_B-R_5|/R_B)\times 100$$

$$X_A=(|R_A-R_5|/R_A)\times 100$$

In the following, the above-mentioned proportions $X_B$ and $X_A$ of the differences may sometimes be referred to as "the 5 minutes fluctuation margins".

By suppressing the fluctuation of the liquid/gas flow rate in the distillation column to be low during the ordinary operation and during the cut operation, in such a manner, it is possible to prevent clogging of the distillation column by polymerization.

Figure 1:
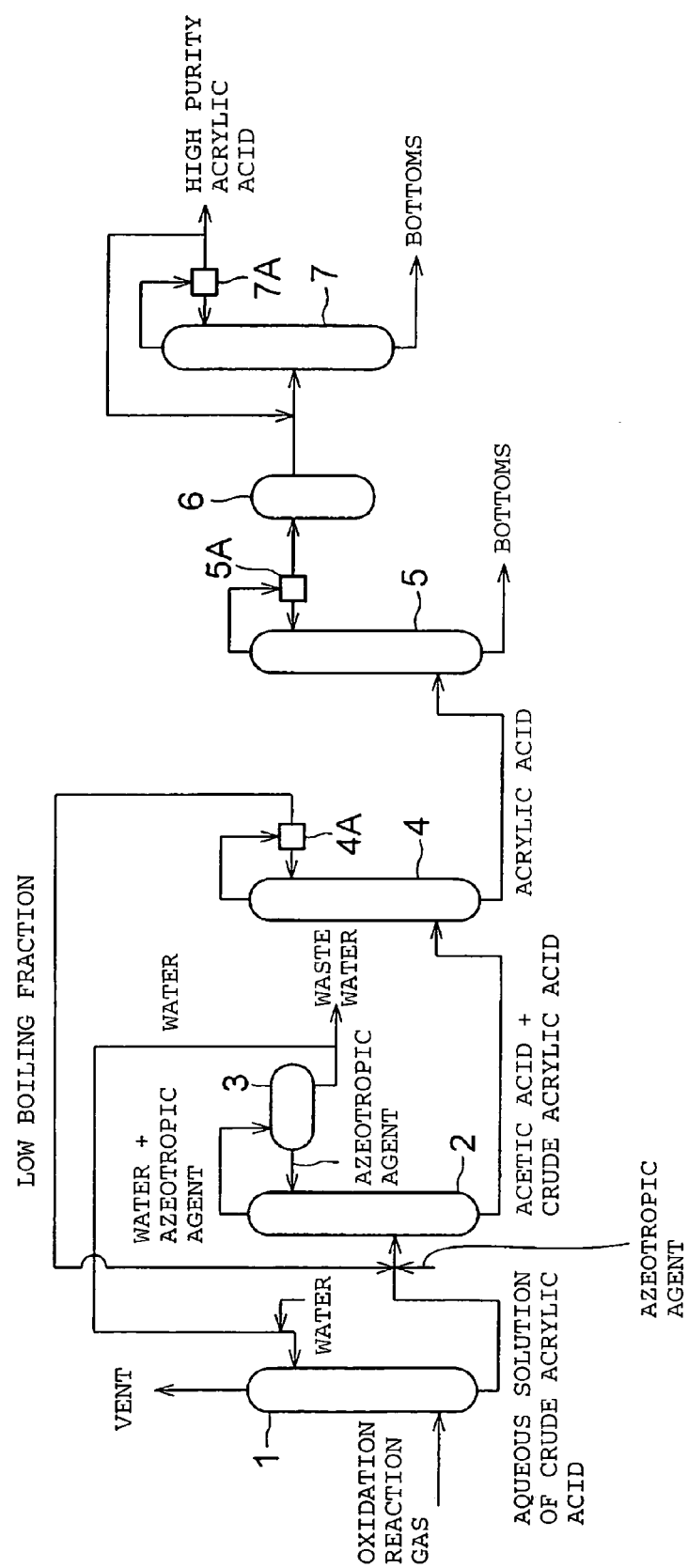
FIG. 1 is a flow chart for the production of acrylic acid showing a practical embodiment of the process for producing (meth)acrylic acid of the present invention.

Meanings of Symbols
1: Acrylic acid collection column
2: Dehydration distillation column
3: Decanter
4: Low boiling separation distillation column 4A, 5A, 7A: Reflux drums
5: High boiling separation distillation column
6: Aldehyde oligomeration reactor
7: Purification distillation column

DETAILED DESCRIPTION OF THE PREFERRED EMBODIMENTS

Now, with reference to the drawings, a practical embodiment of the process for producing (meth)acrylic acid of the present invention will be described in detail.

FIG. 1 is a flow chart for the production of acrylic acid showing a practical embodiment of the process for producing (meth)acrylic acid of the present invention.

An oxidation reaction gas containing acrylic acid obtained by vapor phase catalytic oxidation of propane, propylene and/or acrolein by means of a molecular oxygen-containing gas, is introduced into an acrylic acid collection column 1 and contacted with water to form an aqueous solution of crude acrylic acid. Further, the oxidation reaction gas also contains $N_2$, $CO_2$, acetic acid, water, etc., and a part of acetic acid, $N_2$ and $CO_2$ will be withdrawn as a vent gas from the top of the collection column 1.

The aqueous solution of crude acrylic acid from this collection column 1 will be supplied together with an azeotropic agent to a dehydration distillation column 2. From the column top, an azeotropic mixture comprising water and the azeotropic agent will be distilled, and from the column bottom, crude acrylic acid containing acetic acid will be obtained. The azeotropic mixture comprising water and the azeotropic agent distilled from the top of the dehydration distillation column 2 will be introduced into a decanter 3, wherein it will be separated into an organic phase composed mainly of the azeotropic agent and an aqueous phase composed mainly of water. After an addition of a polymerization inhibitor (not shown), the aqueous phase composed of the azeotropic agent will be recycled to the dehydration distillation column 2. On the other hand, the aqueous phase will be recycled to the acrylic acid collection column 1 and used as collecting water to be contacted with the oxidation reaction gas. Further, if necessary, a part will be discharged out of the system as waste water, and water may be supplemented to a water-returning line. In order to recover the azeotropic agent from the water in the water-returning line, the water may be passed through an azeotropic agent-recovery column (not shown) and then recycled to the acrylic acid collection column 1.

The crude acrylic acid containing acetic acid, withdrawn from the bottom of the dehydration distillation column 2, is introduced into a low boiling separation distillation column 4 to remove the remaining low boiling fraction such as acetic acid, whereby a low boiling fraction such as acetic acid will be separated and removed from the top of the column. The acetic acid from the column top contains acrylic acid, and accordingly, a part will be returned from a reflux drum 4A to the low boiling distillation column 4, and the rest will be returned to the inlet side of the dehydration distillation column 2. This low boiling point fraction containing acetic acid is separated by the dehydration distillation column 2 and finally discharged out of the system as a bent gas via the acrylic acid collection column 1.

From the bottom of the low boiling separation distillation column 4, acrylic acid containing substantially no acetic acid will be obtained. This acrylic acid will be introduced into a high boiling separation distillation column 5, whereby the heavy substances will be separated and removed to obtain purified acrylic acid. The bottoms (high boiling substances) of the high boiling separation distillation column 5 will be introduced into a decomposition reactor (not shown), whereby acrylic acid, etc. formed by the decomposition reaction will be recycled.

Acrylic acid obtained from the high boiling separation distillation column 5 will partially be refluxed to the high boiling separation distillation column 5 via a reflux drum 5A, and the rest may be taken as a product. However, in FIG. 1, in order to oligomerize and separate an aldehyde contained in a very small amount in this purified acrylic acid, the purified acrylic acid is supplied to an aldehyde-oligomerizing reactor 6, whereby an assisting agent such as a thiol is added, and the aldehyde is oligomerized to a heavy substance, and the heavy substance will further be separated and removed in a purification distillation column 7. High purity acrylic acid having the heavy substance of aldehyde removed in the purification distillation column 7 will partially be refluxed to the purification distillation column 7 via a reflux drum 7A, and the rest will be taken out as a product.

In the present invention, in such production of acrylic acid, even in a case where the production rate is reduced by $\alpha\%$ during the cut operation wherein the production rate is reduced than the production rate during the ordinary operation, the liquid/gas flow rate in the distillation column is adjusted to be $(100-\alpha/2)\%$ of the liquid/gas flow rate during the ordinary operation. Namely, usually, in a case where the production rate is reduced by $\alpha$ % than during the ordinary operation, the liquid/gas flow rate in the distillation column will be $(100-\alpha)\%$ of the liquid/gas flow rate during the ordinary operation as the amount of the liquid supplied to the distillation column is reduced. However, in the present invention, the degree of the reduction of the liquid/gas flow rate in the distillation column is controlled to be low so that the flow rate will be at a level of at least $(100-\alpha/2)\%$. If the liquid/gas flow rate in the distillation column during the cut operation is less than $(100-\alpha/2)\%$, clogging by polymerization is likely to result due to an increase in non-uniformity of the liquid/gas dispersion in the distillation column due to the fluctuation of the liquid/gas flow rate. The liquid/gas flow rate in the distillation column during such a cut operation is preferably as close as possible to the liquid/gas flow rate during the ordinary operation, particularly preferably at least $(100-\alpha/3)\%$, further preferably at least $(100-\alpha/10)\%$.

Namely, in a case where the production rate is set to be 70% of the production rate during the ordinary operation ($\alpha=100-70=30\%$), the liquid/gas flow rate in the distillation column is adjusted to be 85 to 100%, preferably from 90 to 100%.

As described above, when operation is carried out at such a liquid/gas flow rate in a case where the production rate during a cut operation is excessively small as compared with the production rate during the ordinary operation, the increase of the quantity of heat of the distillation column required per unit amount of the product will be large, such being not only uneconomical but also likely to lead to a disadvantage such that the amount of the liquid recycled to maintain the liquid/gas flow rate will be excessively large. Accordingly, it is preferred that the present invention is applied to a case where the reduction of the production rate is at most 30% (i.e. $\alpha \leq 30$).

As a method to maintain the liquid/gas flow rate in the distillation column during the cut operation as described above, it is simple and convenient to set the reflux amount to the distillation column to be at a constant level. Further, such a liquid/gas flow rate may be maintained by recycling the liquid withdrawn from the top and/or the bottom of the distillation column to the distillation column and/or a purification step on the upstream side thereof.

Further, it is preferred to carry out the change of the operation condition influential over the liquid/gas flow rate slowly by taking time, in order to minimize the fluctuation of the liquid/gas flow rate in the distillation column due to the change of the production rate. Accordingly, when the amount of the material to be purified, supplied to the distillation column, the amount of the liquid refluxed to the distillation column, or the heat load on the riboiler of the distillation column, is changed, the change per hour (the speed of the change) is preferably set to be at most 5%.

If this speed of the change is fast, the speed of the fluctuation of the liquid/gas flow rate in the distillation column will likewise be fast, whereby the liquid/gas dispersion in the column due to the fluctuation of the liquid/gas flow rate will not reach a constant state, and turbulence of the liquid/gas dispersion in the column will be promoted due to the fluctuation of the liquid/gas flow rate, whereby a polymer is more readily be formed. Once a polymer is deposited in the distillation column, even if the liquid/gas dispersion in the column is subsequently improved, clogging by polymerization in the column will be accelerated.

Further, during the ordinary operation wherein the production rate is constant, even if the average liquid/gas flow rate per hour in the distillation column is constant, there is a fluctuation in a short period of time. In order to prevent formation of a polymer, such a fluctuation is also desired to be sufficiently small, and for this purpose, the five minutes fluctuation margins $X_B$ and $X_A$ of the heat load on the riboiler of the distillation column are preferably at most 10%.

As a method for stabilizing the heat load on the riboiler, there may, for example, be mentioned a method of reducing control parameters by setting the reflux liquid amount or the column bottom/top withdrawal amount to be at a constant level, or a method wherein in a case where the heat source is steam, the supply temperature of steam is maintained to be constant by controlling the pressure before the supply to the riboiler.

In the present invention, the acrylic acid-containing material to be purified, which is supplied to the distillation column in which the liquid/gas flow rate is controlled, is an aqueous solution of crude acrylic acid obtained by collecting the acrylic acid-containing gas obtained by vapor phase catalytic oxidation of propane, propylene and/or acrolein by means of molecular oxygen, by water or an organic solvent forming double liquid layers with water, or a liquid and/or gas containing at least 30 wt % of acrylic acid, which forms in a step of separating and purifying acrylic acid from the aqueous solution of crude acrylic acid to obtain a product. Namely, for example, in the process for producing acrylic acid shown in FIG. 1, the present invention can be applied to every distillation column such as the dehydration distillation column 2, the low boiling separation distillation column 4, the high boiling separation distillation column 5 or the purification distillation column 7.

Further, the distillation process for purifying acrylic acid is not limited to the one shown in FIG. 1, and, for example, there may be one wherein the functions of the dehydration distillation column and the low boiling separation distillation column in FIG. 1 are combined in one column, and the present invention can be applied to such a distillation column. Further, there is a process wherein acrylic acid is extracted by an extracting solvent from the aqueous solution of crude acrylic acid, and acrylic acid is separated from the extract solution and purified. The present invention is applicable also to the distillation column in such a process.

The type of such a distillation column is not particularly limited, and a plate column or packed column may, for example, be mentioned.

Further, for the distillation purification of acrylic acid, it is preferred to employ a commonly employed method for preventing polymerization, specifically, a method of lowering the operation temperature under a reduced pressure and adding a polymerization inhibitor. Further, it is preferred that the bottom temperature of the distillation column is maintained to be at most 100° C. The polymerization inhibitor is preferably supplied at least from the top of the column. Further, molecular oxygen may also be supplied from the bottom of the distillation column.

In the foregoing, the production of acrylic acid has been described. However, the present invention is likewise applicable to a process for producing methacrylic acid by vapor phase catalytic reaction of isobutylene and/or t-butyl alcohol.

Now, the present invention will be described in further detail with reference to Examples and Comparative Examples.

EXAMPLE 1

In the process for producing acrylic acid shown in FIG. 1, the production of acrylic acid was carried out in accordance with the process of the present invention.

Propylene was subjected to vapor phase catalytic oxidation in the presence of molecular oxygen and a solid catalyst to obtain an oxidation reaction gas containing acrylic acid, which is collected in the acrylic acid collection column 1 with an aqueous solution containing 6 wt % of acetic acid to obtain an aqueous solution containing crude acrylic acid. This aqueous solution of crude acrylic acid contained 35 wt % of water, 3 wt % of acetic acid and 1 wt % of formaldehyde.

This aqueous solution of crude acrylic acid was supplied to an intermediate plate of the dehydration distillation column 2 comprising 30 plates, whereby azeotropic dehydration distillation with toluene was carried out. The toluene was used in an amount of 8.5 times by volume to the amount of water to be distilled off by distillation, and the operation was carried out at the column top temperature of 43° C. and at the column top pressure of 14 kPa. During a cut operation, the production rate for acrylic acid was reduced by 25% than the ordinary operation, and by the change in the production rate for acrylic acid, the amount of the liquid supplied to the distillation column 2 was reduced to 75% in proportion thereto, but by adjusting the toluene reflux amount to be constant irrespective of the production rate, the fluctuation of the liquid/gas flow rate in the column was controlled within a range of from 87.5 to 100%, whereby it was possible to carry out continuous operation constantly for one year. The increase in the pressure difference within the dehydration distillation column 2 after the continuous operation for one year relative to the initial stage of the operation, was 1.6 kPa, and thus, it was confirmed that there was no problem of clogging by polymerization.

COMPARATIVE EXAMPLE 1

The operation was carried out in the same manner as in Example 1 except that the toluene reflux amount was in proportion to the amount of the liquid supplied to the distillation column. The change in the production rate during the operation period was carried out within a range of from 80 to 100%, and the liquid/gas flow rate in the distillation column was changed from 80 to 100% also in proportion thereto. As a result, the pressure difference in the column after the operation for three months increased to 3.9 kPa, whereby it became impossible to continue the operation.

EXAMPLE 2

In Example 1, crude acrylic acid obtained from the dehydration distillation column 2 was separated into a low boiling fraction and a high boiling fraction in the subsequent two distillation columns 4 and 5, respectively. Further, in an aldehyde-oligomerization reactor 6, thiol was added to convert the contained aldehyde into a heavy substance, and then, the product was supplied to an intermediate stage of the purification distillation column 7 and distilled. The liquid supplied to the purification column 7 contained 1000 weight ppm of unreacted thiol, 120 weight ppm of maleic acid and 500 weight ppm of thioacetal. In this purification distillation column 7, IMTP (Interlox Metal Tower Packing, manufactured by Norton Company) was packed as an irregular packing material, and the operation was carried out at a column top temperature of 50° C. at a reflux ratio of 1.0.

The production rate for acrylic acid was changed within a range of from 70 to 100%. However, when the production rate was reduced, a part of acrylic acid obtained from the top of the distillation column 7 was recycled to the supply line of the distillation column 7, to maintain the liquid/gas flow rate in the distillation column 7 to be always constant (100%). Further, the temperature of steam supplied as a heat source to the riboiler was maintained within a range of ±5° C., whereby the fluctuation of the supplied heat quantity was suppressed, and the five minutes fluctuation margin was maintained within 6%.

As a result, it was possible to carry out continuous operation constantly for one year. The increase in the pressure difference in the purification distillation column 7 during this period, was 0.4 kPa, and thus, it was confirmed that there was no problem of clogging by polymerization.

EXAMPLE 3

The operation was carried out in the same manner as in Example 2, except that no temperature control of the steam supplied to the riboiler was carried out. Due to the fluctuations of the temperature of the steam and the flow rate, the five minute fluctuation margin of the supplied heat quantity was 16% at the maximum.

As a result, it was possible to carry out continuous operation constantly for a half year, and the increase in the increase in the pressure difference in the purification distillation column 7 during this period, was 0.7 kPa.

COMPARATIVE EXAMPLE 2

The operation was carried out in the same manner as in Example 3, except that the reflux ratio was fixed to 1.0 without recycling acrylic acid from the top of the purification distillation column to the supply line. The production rate for acrylic acid changed within a range of from 80 to 95% relative to the ordinary operation, whereby the liquid/gas flow rate in the purification distillation column likewise changed within this range. Further, the speed of the change in the amount of the liquid supplied to the purification distillation column along with the change in the production rate was 8%/30 minutes at the maximum.

As a result, the pressure difference in the purification distillation column after the operation for six weeks increased to 3.0 kPa, whereby it became impossible to continue the operation.

COMPARATIVE EXAMPLE 3

The operation was carried out in the same manner as in Comparative Example 2, except that the speed of the change in the amount of the liquid supplied to the purification distillation column along with the change in the production rate was 8%/30 minutes at the maximum.

The pressure difference in the purification distillation column after the operation for three months increased to 3.0 kPa, whereby it became impossible to continue the operation.

EXAMPLE 4

The operation was carried out in the same manner as in Example 3, except that acrylic acid obtained from the top of the distillation column 7 was not recycled to the supply line of the distillation column 7, and the reflux amount to the distillation column 7 was fixed to 100% of the production rate. The production rate for acrylic acid at that time was changed within a range of from 78 to 100%, whereby the fluctuation of the liquid/gas flow rate in the purification distillation column was within a range of from 89 to 100%.

As a result, it was possible to carry out continuous operation constantly for a half year, and the increase in the pressure difference in the purification distillation column during this period was 1.5 kPa.

INDUSTRIAL APPLICABILITY

According to the present invention, it is possible to prevent clogging of a distillation column by polymerization, in a plant for producing (meth)acrylic acid accompanying a change in the production rate of (meth)acrylic acid, and thereby carry out a stabilized and efficient production of (meth)acrylic acid over a long period.

The entire disclosure of Japanese Patent Application No. 2001-381867 filed on Dec. 14, 2001 including specification, claims, drawings and summary is incorporated herein by reference in its entirety.

What is claimed is:

1. A process for producing (meth)acrylic acid, which comprises purifying a (meth)acrylic acid-containing material to be purified, wherein said purifying comprises distilling said (meth)acrylic acid containing material in a distillation column, wherein during a cut operation in which a production rate of (meth)acrylic acid is reduced by α% relative to a production rate of (meth)acrylic acid prior to said cut operation, a liquid/gas flow rate in the distillation column is adjusted to be at least (100−α/2)% of the liquid gas flow rate prior to said cut operation, wherein a fluctuation margin of a heat load on a reboiler of the distillation column prior to said cut operation is a fluctuation margin such that proportions $X_B$ and $X_A$ of the differences between an average value $R_5$ of a heat load during optional 5 minutes and an average value $R_B$ of a heat load during one hour before the 5 minutes and between $R_5$ and an average value $R_A$ of a heat load for one hour after the 5 minutes, as calculated by the following formulae, are at most 10%:

$$X_B=(|R_B-R_5|/R_B)\times100$$

$$X_A=(|R_A-R_5|/R_A)\times100.$$

2. The process for producing (meth)acrylic acid according to claim 1, wherein a liquid withdrawn from a top and/or the bottom of the distillation column is recycled to the distillation column on an upstream side thereof.

3. The process for producing (meth)acrylic acid according to claim 1, wherein during the cut operation in which the production rate of (meth)acrylic acid is reduced by α%, the liquid/gas flow rate in the distillation column is adjusted to be at least (100−α/3)% of the liquid/gas flow rate prior to said cut operation.

4. The process for producing (meth)acrylic acid according to claim 1, wherein when an amount of the material to be purified, supplied to the distillation column, an amount of a liquid refluxed to the distillation column, or a heat load on a reboiler side of the distillation column, is changed, the change per hour is at most ±5%.

5. The process for producing (meth)acrylic acid according to claim 1, wherein α is at most 30.

6. The process for producing (meth)acrylic acid according to claim 2, wherein α is at most 30.

7. The process for producing (meth)acrylic acid according to claim 3, wherein α is at most 30.

8. The process for producing (meth)acrylic acid according to claim 4, wherein α is at most 30.

9. The process for producing (meth)acrylic acid according to claim 2, wherein during the cut operation in which the production rate of (meth)acrylic acid is reduced by α%, the liquid/gas flow rate in the distillation column is adjusted to be at least (100−α/3)% of the liquid/gas flow rate during the ordinary operation.

10. The process for producing (meth)acrylic acid according to claim 4, wherein during the cut operation in which the production rate of (meth)acrylic acid is reduced by α%, the liquid/gas flow rate in the distillation column is adjusted to be at least (100−α/3)% of the liquid/gas flow rate during the ordinary operation.

11. The process for producing (meth)acrylic acid according to claim 5, wherein during the cut operation in which the production rate of (meth)acrylic acid is reduced by α%, the liquid/gas flow rate in the distillation column is adjusted to be at least (100−α/3)% of the liquid/gas flow rate during the ordinary operation.

12. The process for producing (meth)acrylic acid according to claim 2, wherein when an amount of the material to be purified, supplied to the distillation column, an amount of a liquid refluxed to the distillation column, or a heat load on a reboiler side of the distillation column, is changed, the change per hour is at most ±5%.

13. The process for producing (meth)acrylic acid according to claim 3, wherein when an amount of the material to be purified, supplied to the distillation column, an amount of a liquid refluxed to the distillation column, or a heat load on a reboiler side of the distillation column, is changed, the change per hour is at most ±5%.

14. The process for producing (meth)acrylic acid according to claim 1, wherein when an amount of the material to be purified, supplied to the distillation column, an amount of a liquid refluxed to the distillation column, or a heat load on a reboiler side of the distillation column, is changed, the change per hour is at most ±5%.

* * * * *